US010772861B2

(12) United States Patent
Schmid-Schonbein et al.

(10) Patent No.: US 10,772,861 B2
(45) Date of Patent: *Sep. 15, 2020

(54) ADMINISTRATION OF SERINE PROTEASE INHIBITORS TO THE STOMACH

(71) Applicants: Leading Biosciences, Inc., Carlsbad, CA (US); The Regents of the University of California, Oakland, CA (US)

(72) Inventors: Geert W. Schmid-Schonbein, Del Mar, CA (US); Yung-Tsai (Andrew) Lee, Taipei (TW); Jeng Wei, Taipei (TW)

(73) Assignees: Leading Biosciences, LLC, Carlsbad, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/197,956

(22) Filed: Nov. 21, 2018

(65) Prior Publication Data

US 2019/0175532 A1 Jun. 13, 2019
US 2020/0246291 A9 Aug. 6, 2020

Related U.S. Application Data

(60) Continuation of application No. 15/335,242, filed on Oct. 26, 2016, now Pat. No. 10,137,100, which is a division of application No. 13/825,779, filed as application No. PCT/US2011/053019 on Sep. 23, 2011, now Pat. No. 9,504,736.

(60) Provisional application No. 61/529,052, filed on Aug. 30, 2011, provisional application No. 61/385,798, filed on Sep. 23, 2010.

(51) Int. Cl.
| | |
|---|---|
| A61K 31/195 | (2006.01) |
| A61K 31/765 | (2006.01) |
| A61K 31/185 | (2006.01) |
| A61K 31/19 | (2006.01) |
| A61K 31/24 | (2006.01) |
| A61K 38/57 | (2006.01) |
| A61K 9/00 | (2006.01) |
| A61K 31/10 | (2006.01) |
| A61K 31/145 | (2006.01) |
| A61K 31/155 | (2006.01) |
| A61K 31/216 | (2006.01) |
| A61K 31/661 | (2006.01) |
| A61K 38/17 | (2006.01) |
| A61K 47/02 | (2006.01) |
| A61K 47/10 | (2017.01) |
| A61K 9/08 | (2006.01) |

(52) U.S. Cl.
CPC .......... *A61K 31/195* (2013.01); *A61K 9/0053* (2013.01); *A61K 31/10* (2013.01); *A61K 31/145* (2013.01); *A61K 31/155* (2013.01); *A61K 31/185* (2013.01); *A61K 31/19* (2013.01); *A61K 31/216* (2013.01); *A61K 31/24* (2013.01); *A61K 31/661* (2013.01); *A61K 31/765* (2013.01); *A61K 38/1722* (2013.01); *A61K 38/57* (2013.01); *A61K 47/02* (2013.01); *A61K 47/10* (2013.01); *A61K 9/08* (2013.01)

(58) Field of Classification Search
CPC ... A61K 31/195; A61K 31/765; C07C 229/46
See application file for complete search history.

(56) References Cited

U.S. PATENT DOCUMENTS

| | | | |
|---|---|---|---|
| 4,465,662 | A | 8/1984 | Sato et al. |
| 5,962,405 | A | 10/1999 | Seelich |
| 6,017,881 | A | 1/2000 | Ammons et al. |
| 6,121,232 | A | 9/2000 | Nur et al. |
| 6,350,459 | B1 | 2/2002 | Suzuki |
| 6,534,283 | B1 | 3/2003 | Schmid-Schoenbein et al. |
| 6,708,822 | B1 | 3/2004 | Muni |
| 6,939,559 | B1 | 9/2005 | Nishibe et al. |
| 7,169,381 | B2 | 1/2007 | Barras |
| 7,235,247 | B2 | 6/2007 | Nishibe et al. |
| 7,276,235 | B2 | 10/2007 | Metzner et al. |
| 8,252,302 | B2 | 8/2012 | Macdonald |
| 8,541,371 | B2 | 9/2013 | Schmid-Schonbein et al. |
| 8,957,113 | B2 | 2/2015 | Moore et al. |

(Continued)

FOREIGN PATENT DOCUMENTS

| | | |
|---|---|---|
| CN | 103054861 A | 4/2013 |
| CN | 103099800 A | 5/2013 |

(Continued)

OTHER PUBLICATIONS

Altshuler et al. Transmural intestinal wall permeability in severe ischemia after enteral protease inhibition. PLoS One 9(5)e96655 (2014).

(Continued)

*Primary Examiner* — Jeffrey E. Russel
(74) *Attorney, Agent, or Firm* — Edward D. Grieff; Mintz, Levin, Cohn, Ferris, Glovsky and Popeo, P.C.

(57) ABSTRACT

The inventors have unexpectedly discovered that shock and/or potential multi-organ failure due to shock can be effectively treated by administration of liquid high-dose protease inhibitor formulations to a location upstream of where pancreatic proteases are introduced into the gastrointestinal tract. Most preferably, administration is directly to the stomach, for example, via nasogastric tube under a protocol effective to treat shock by such administration without the need of providing significant quantities of the protease inhibitor to the jejunum and/or ileum.

20 Claims, 2 Drawing Sheets

(56) References Cited

U.S. PATENT DOCUMENTS

| | | | |
|---|---|---|---|
| 9,278,077 | B2 | 3/2016 | DeBrouse |
| 9,314,442 | B2 | 4/2016 | Hallam et al. |
| 9,504,736 | B2 | 11/2016 | Schmid-Schonbein et al. |
| 9,775,821 | B2 | 10/2017 | Hallam et al. |
| 10,137,100 | B2 | 11/2018 | Schmid-Schonbein et al. |
| 2002/0001584 | A1 | 1/2002 | Metzner et al. |
| 2003/0144212 | A1 | 7/2003 | Hoffman et al. |
| 2004/0018984 | A1 | 1/2004 | Miyazaki |
| 2006/0198817 | A1 | 9/2006 | Alverdy |
| 2007/0059272 | A1 | 3/2007 | Alverdy |
| 2008/0194611 | A1 | 8/2008 | Alverdy |
| 2008/0206188 | A1 | 8/2008 | Alverdy et al. |
| 2009/0017114 | A1 | 1/2009 | Heasley et al. |
| 2009/0186949 | A1 | 7/2009 | Alverdy et al. |
| 2009/0324736 | A1 | 12/2009 | Johnson et al. |
| 2010/0179091 | A1 | 7/2010 | Schmid-Schonbein et al. |
| 2011/0060040 | A1 | 3/2011 | Virsik et al. |
| 2012/0078017 | A1 | 3/2012 | Alverdy et al. |
| 2012/0316190 | A1 | 12/2012 | Alverdy et al. |
| 2013/0310325 | A1 | 11/2013 | Schmid-Schonbein et al. |
| 2014/0018293 | A1 | 1/2014 | Delano et al. |
| 2014/0271923 | A1 | 9/2014 | Reid |
| 2015/0290157 | A1 | 10/2015 | Moore et al. |
| 2015/0297619 | A1 | 10/2015 | Schmid-Schonbein et al. |
| 2017/0231935 | A1 | 8/2017 | Schmid-Schonbein et al. |

FOREIGN PATENT DOCUMENTS

| | | |
|---|---|---|
| CN | 103565743 A | 2/2014 |
| EP | 1567117 B1 | 2/2012 |
| JP | 6-219942 A | 8/1994 |
| JP | 2003-128540 A | 5/2003 |
| JP | 2005-068076 A | 3/2005 |
| JP | 2007-284423 A | 11/2007 |
| JP | 2009-019008 A | 1/2009 |
| WO | WO-1999/08514 A1 | 2/1999 |
| WO | WO-2001/37854 A1 | 5/2001 |
| WO | WO-2004/047778 A1 | 6/2004 |
| WO | WO-2006/073430 A2 | 7/2006 |
| WO | WO-2006/073430 A3 | 7/2006 |
| WO | WO-2006/132963 A2 | 12/2006 |
| WO | WO-2006/132963 A3 | 12/2006 |
| WO | WO-2007/053194 A2 | 5/2007 |
| WO | WO-2007/053194 A3 | 5/2007 |
| WO | WO-2007/101264 A2 | 9/2007 |
| WO | WO-2007/101264 A3 | 9/2007 |
| WO | WO-2009/045543 A1 | 4/2009 |
| WO | WO-2009/132149 A2 | 10/2009 |
| WO | WO-2009/132149 A3 | 10/2009 |
| WO | WO-2009/137672 A1 | 11/2009 |
| WO | WO-2010/087874 A1 | 8/2010 |
| WO | WO-2012-040595 A2 | 3/2012 |
| WO | WO-2012-040595 A9 | 3/2012 |
| WO | WO-2012-045083 A2 | 4/2012 |
| WO | WO-2012-045083 A3 | 4/2012 |
| WO | WO-2013/093164 A1 | 6/2013 |
| WO | WO-2014/028052 A1 | 2/2014 |
| WO | WO-2015/148474 A1 | 10/2015 |

OTHER PUBLICATIONS

Altshuller. Degrading Proteases and Organ Failure during Physiological Shock. Thesis 2013.

Altshuller et al. Poster—Development of Strategies to Minimize Autodigestion and Death: Methods to Preserve the Barrier of an Ischemic Intestine. UCSD Jacobs School of Engineering Research Expo. Apr. 18, 2013.

Chang et al. Breakdown of mucin as barrier to digestive enzymes in the ischemic rat small intestine. PLos One 7(6):e40087 (2012).

Chang et al. Disruption of the mucosal barrier during gut ischemia allows entry of digestive enzymes into the intestinal wall. Shock 37(3):297-305 (2012).

Delano, F.A. et al. (Apr. 2009). "Blockade of Pancreatic Digestive Proteases in Severe Hemorrhagic Shock Enhances Long-term Survival Rate," *Experimental Biology Annual Meeting* 23:594.13.

Delano et al. Pancreatic digestive enzyme blockade in the intestine increases survival after experimental shock. Sci Transl Med 5(169):169ra11 (2013).

Delano et al. Pancreatic digestive enzyme blockade in the small intestine prevents insulin resistance in hemorrhagic shock. Shock 41(1):55-61 (2014).

GoLYTELY Product Insert (2013).

Habler, O. et al. (Aug. 2005). "Artificial oxygen carriers as an alternative to red blood cell transfusion," Anaesthesist 54(8):741-754. (Translation of Abstract only).

Kim, et al., "Inhibition of Intraluminal Pancreatic Enzymes With Nafamostat Mesilate Improves Clinical Outcomes After Hemorrhagic Shock in Swine," Injury, Infection, and Critical Care, vol. 68, No. 5, 1078-83 (May 2010).

Lee et al. Successful treatment with continuous enteral protease inhibitor in a patient with severe septic shock. Transplant Proc 44(3):817-819 (2012).

Mitsuoka, et al., "Generation of in vivo activating factors in the ischemic intestine by pancreatic enzymes," PNAS, vol. 97, No. 4, 1772-77 (Feb. 15, 2000).

Mooney, R.A. et al. (1976). "Prevention of peritoneal adhesions with aprotinin (trasylol)," *J Int Med Res* 495):360-363.

PCT/US2015/022198 International Search Report and Written Opinion dated Jun. 15, 2015.

PCT/US2011/053019 International Preliminary Report on Patentability dated Apr. 4, 2013.

PCT/US2011/053019 International Search Report and Written Opinion dated Apr. 10, 2012.

U.S. Appl. No. 14/666,926 Office Action dated Jul. 24, 2015.

U.S. Appl. No. 13/825,779 Office Action dated Apr. 2, 2015.

U.S. Appl. No. 13/825,779 Office Action dated Sep. 26, 2014.

Wu, L. et al., "High-Molecule-Weigh Polyethylene Glycol Prevents Lethal Sepsis Due to Intestinal Pseudomonas aeruginosa", Gastronterology, vol. 126, 488-498, 2004.

Lan Wang et al. (2009). "Use of glucose-electrolyte effervescent in autumn diarrhea diseases," located at <http://big.hi138.com/yiyao/yaoxue/200908/132939.asp>, 3 pages. (Translation of Abstract only).

Omega Standard et al. (Aug. 30, 2012). "Product Monograph, Tranexamic Acid Injection 100 mg/mL," 16 pages.

Hu Sen (2002). "Effects of Enteral Nutrients on Gut Mucosal Blood Flow Following Hemorrhagic Shock and Resuscitation," Amino Acids & Biotic Resources (24):39-41. (abstract only).

Xu Hui et al. (1988). "Inhibition of Glucose Infusion on Hemorrhagic Shock Decompensation Stage," International Journal of Orthopaedics vol. 3 Clinical Gastrointestinal Endoscopy-Ginsburg-p. 103;Table 8-1.

GoLYTELY Highlights of Prescribing Information (Jan. 16, 2014). 2 pages.

Kozar, R.A. et al. (Jul.-Aug. 2002). "Specific intraluminal nutrients alter mucosal blood flow during gut ischemia/reperfusion," *JPEN J Parenter Enteral Nutr* 26(4):226-229.

ADMINISTRATION OF SERINE PROTEASE INHIBITORS TO THE STOMACH

RELATED APPLICATIONS

This application is a continuation of U.S. application Ser. No. 15/335,242 filed Oct. 26, 2016, issued as U.S. Pat. No. 10,137,100, which is a divisional of U.S. application Ser. No. 13/825,779 filed Aug. 2, 2013, issued as U.S. Pat. No. 9,504,736, which is a § 371 national stage of PCT/US2011/53019, filed Sep. 23, 2011, which claims priority to U.S. Application No. 61/385,798 filed Sep. 23, 2010, and U.S. Application No. 61/529,052, filed Aug. 30, 2011.

FIELD OF THE INVENTION

The field of the invention is compositions and methods of treating shock.

BACKGROUND OF THE INVENTION

Shock is a life-threatening complication in situations associated with trauma including burns, surgery, ischemia, sepsis, and other critical care applications. Shock is a broad term that describes a group of circulatory syndromes, all of which result in general cellular hypoxia, and ultimately lead to irreversible cardiovascular collapse because of their combined effects on the microcirculation.

Shock is a multifaceted systemic response to any of a number of stress inducing stimuli that results in cellular activation and release of a number of interacting response mediators, including cytokines, inflammatory and immune mediators, and nitric oxide (NO). During an immune response, oxygen free radicals and superoxides are generated to kill pathogens. However, oxygen free radicals and superoxides are also damaging to the host cells, resulting in oxidation of lipids, proteins and nucleic acids. The mediators of shock orchestrate complex biological interactions and amplification of signals that result in a systemic response to a localized insult.

Due to the multifaceted nature of factors inducing shock, development of therapeutics has been difficult. Most therapies have focused on the modulation of a single factor (e.g. cytokines, NO, endotoxin) to mitigate the effects of shock. Unfortunately, inhibition of any one of these pleiotropic factors is ineffective. Organ specific therapies can support life, but are not an ideal option as they often sacrifice remote organ function.

One potential therapeutic molecule that has been suggested for use in shock is the bactericidal/permeability-increasing protein (BPI), a protein involved in the immune response (Ammons, U.S. Pat. No. 6,017,881). Intestinal ischemia, frequently associated with shock, results in the breakdown of the intestinal mucosal permeability barrier allowing for the translocation of bacteria and/or endotoxin from the intestinal lumen to the vascular system. During shock, endotoxin has been detected in the portal vein, but its role in shock has not been clearly defined. BPI is a protein typically isolated from granules of mammalian polymorphonuclear cells (PMNs). PMNs are blood cells involved in the defense of the body against invading microorganisms. BPI is highly specific for gram negative bacteria and seems to have no deleterious effects on other pathogens or host cells. Administration of BPI to rats results in a decrease in the adverse physiological effects of intestinal ischemia which may catalyze the other symptoms of shock. However BPI only affects one of the pathways that are activated in shock, so it is of limited use. Additionally, BPI acts by attacking the endotoxin and bacteria after they have been released from the intestine into the bloodstream; therefore, it cannot be used to prevent the occurrence of shock.

In another approach, the inventors demonstrated the role of pancreatic proteases in shock and protective effects of certain uses of protease inhibitors as described in U.S. Pat. No. 6,534,283. Pancreatic enzymes are released normally into the small intestine for digestion with no adverse effects. However, during shock, the intestinal permeability barrier is compromised, and the inventors therefore theorized that protease susceptible sites not present under normal conditions are revealed, tissues are broken down, and proteolytic products that are strong activators of shock are released. A variety of so formed proteolytic products can act as mediators of shock, and the inventors consequently considered that shock is most effectively treated by preventing in the small intestine protease activation or by the inhibition or elimination of the proteases in the small intestine that generate the activators of shock. To that end, the inventors believed that administration of protease inhibitors directly into the small intestine would prevent shock in rats as determined by both survival time and molecular and histological analysis.

However, while experimental observations seemed to confirm at least certain effects of protease inhibitors (e.g., inhibition of the activation of circulating neutrophils, attenuated myeloperoxidase activity), the inventors only considered possible prophylactic intervention using administration of protease inhibitors directly to the small intestine.

Thus, even though there are various methods for treatment or prophylaxis of shock known in the art, there is still a need to provide effective methods and compositions for treatment of shock and shock associated conditions.

SUMMARY OF THE INVENTION

The inventors now have unexpectedly discovered that shock and/or potential multi-organ failure due to shock can be effectively treated by administration of liquid high-dose protease inhibitor formulations to a location upstream of where pancreatic proteases are introduced into the gastrointestinal tract. Most preferably, administration is directly to the stomach, for example, via nasogastric tube under a protocol effective to treat shock by such administration without the need of providing significant quantities of the protease inhibitor to the jejunum and/or ileum. Thus, intervention in developing or acute shock is now possible in a rapid, simple, and effective manner.

In one aspect of the inventive subject matter, a method of treating shock and/or potential multi-organ failure due to shock in a mammal in which in one step the mammal is diagnosed as having a shock condition. In another step, a therapeutically effective amount of a protease inhibitor is administered (typically in a liquid formulation) at a dosage of at least 20 mg/kg, wherein the liquid formulation is administered to a location upstream of a location at which pancreatic proteases are released into the gastrointestinal tract, and wherein the liquid formulation is administered under a protocol effective to treat the shock and potential multi-organ failure from the location. Thus, it should be appreciated that treatment of shock can be initiated and sustained without administration of significant quantities of protease inhibitors to the small intestine.

Consequently, it is generally preferred that the location is the stomach and that the administration is performed via a nasogastric tube or a catheter. Alternatively, administration may also be done via an oral solution or direct injection. While it is generally preferred that administration is performed using a single undivided dose per day, multiple divided doses are also deemed suitable. Moreover, it is further preferred that administration is done, optionally in divided daily doses, over at least two days, most preferably at least seven days, and most preferably at least ten days.

In further contemplated aspects of the inventive subject matter, the dosage is at least 25 mg/kg, or at least 50 mg/kg, or at least 100 mg/kg. Thus, suitable liquid formulations may include the protease inhibitor at a concentration of between 0.5 mM and 50 mM. Viewed from another perspective, administration may be performed at a daily dosage of between 2 g to 20 g.

Most typically, the protease inhibitor in the liquid formulation is a serine protease inhibitor, and/or maybe tranexamic acid, FOY, ANGD, camostate, an alpha-1 antitrypsin, a serpine, and/or an MMP protease inhibitor. Where desirable, a second protease inhibitor formulation may be administered to the mammal. Such second protease inhibitor formulation may then include a protease inhibitor that is the same (or different) protease inhibitor as that in the liquid formulation. Additionally, it is contemplated that an oxygen carrier may be administered to the mammal in an amount effective to reduce organ damage due to shock. While numerous types of shock are contemplated, especially contemplated shock conditions include traumatic shock, septic shock, cardiogenic shock, and hypovolemic shock. Thus, diagnosis of the shock condition may vary considerably. However, it is generally preferred that the diagnosing the shock condition includes measurement of a blood amylase and/or a blood protease activity.

In one especially preferred aspect of the inventive subject matter, the mammal is a human, the protease inhibitor is FOY, and the dosage of the protease inhibitor is at least 25 mg/kg. Most preferably, administration will be (once) daily administration of the liquid formulation for at least seven days, typically performed via nasogastric tube.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1A:
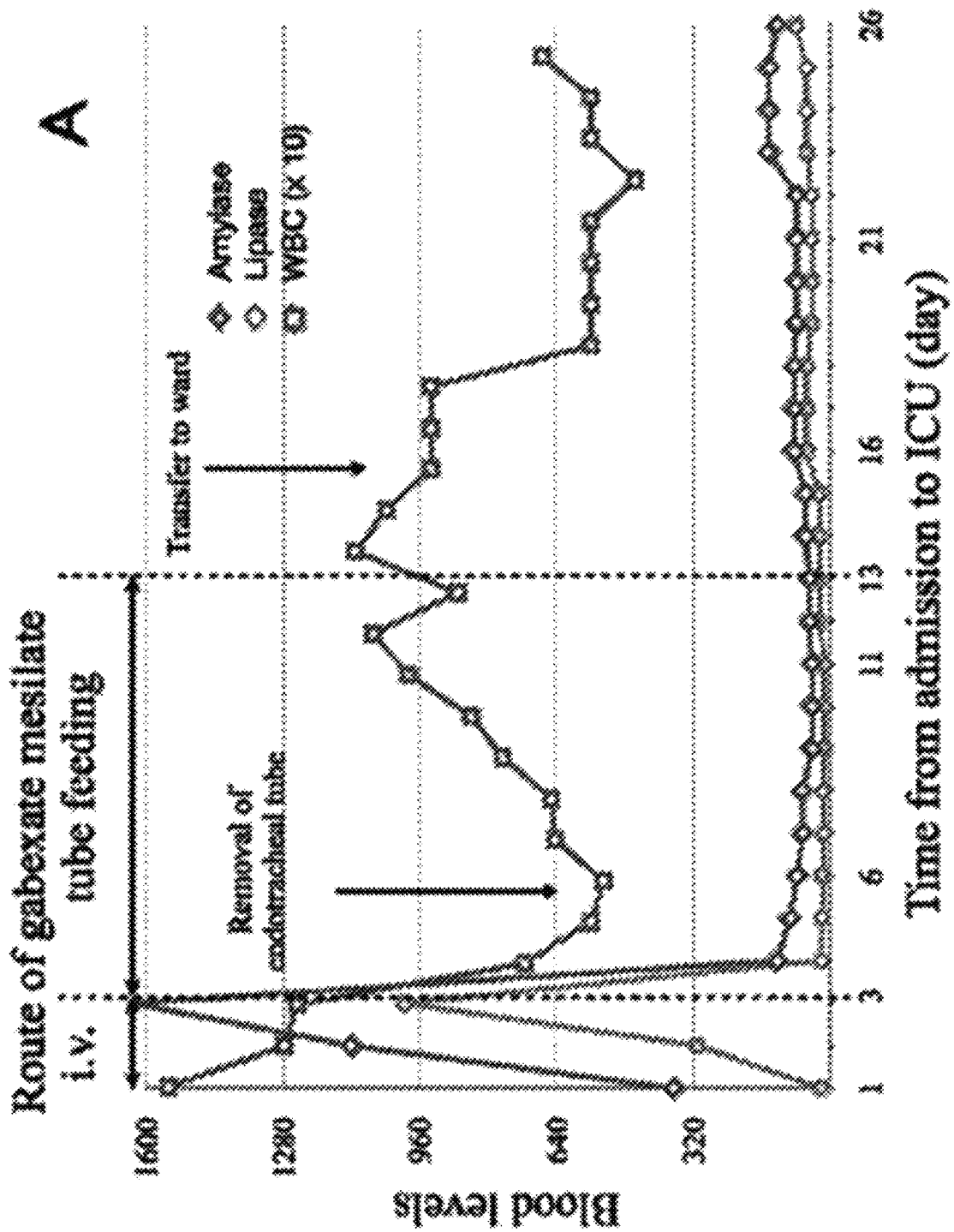
FIG. 1A is a graph depicting time course of white blood cell (WBC) count, amylase and lipase activity before and during treatment of a human patient according to the inventive subject matter.

The inventors have unexpectedly discovered that various protease inhibitors may be administered in a significantly simpler manner and at a high concentration to effectively treat a developing or acute shock condition and/or multi-organ failure due to shock. Preferably, the administration of protease inhibitors is directly into the stomach, and most preferably via nasogastric tube, oral solution, catheter, or direct injection at a dosage range of typically between 10-100 mg/kg. Such administration will not only result in rapid and simple delivery of the protease inhibitor to the patient, but surprisingly also allows for onset and maintenance of treatment without the need to provide substantial quantities to the small intestine.

Remarkably, adverse effects expected from the shock condition were not observed in all subjects treated. Based on the above, the inventors therefore expect that shock conditions can be prevented, ameliorated, or reversed using administration of protease inhibitors at very high concentrations (significantly above 10 mg/ml) via oral administration or administration via NG tube.

In contrast, it should be noted that U.S. Pat. No. 6,534,283, which is incorporated in its entirety by reference herein, taught administration of certain proteases at very low dosages directly into the intestine. For example, prophylactic treatment for the prevention of shock during cardiac surgery was contemplated to require one to eight hours prior to surgery administration of 6-amidino-2-naphthyl p-guanidinobenzoate dimethanesulphonate (ANGD) orally at a dose of 0.1 to 1.0 mg/kg/hr, to a fasting patient to inhibit pancreatic proteases in the intestine. Prior to surgery, ANDG was contemplated to be given by IV drip at 0.1-1.0 mg/kg/hr.

Similarly, intestinal lavage for the prevention of shock during abdominal surgery was contemplated to be performed via a catheter that is inserted directly into the intestine, and the intestine is flushed with a saline solution supplemented with glutathione and 0.5 to 5.0 mg/kg/hr [Ethyl p-(6-guanidinohexanoyloxy) benzoate] methanesulfonate (FOY), at 1.5 to 2.5 mg/kg/hr at a flow rate of 50 to 200 ml/min for at least 5 minutes prior to and during subsequent surgical procedures.

In yet further examples in the '283 patent, it was contemplated that in traumatic shock alpha-2 macroglobulin is administered IV and in the case of suspected intestinal or pancreatic injury, protease inhibitors will be administered via an esophageal tube directly into the stomach at a 1-10 mg/kg initial dose for the prevention of shock. Likewise, a combination of oral prophylaxis and intestinal lavage for the prevention of shock during surgery was contemplated. Here, anti-trypsin is administered orally preferably at a dose of 0.1 to 10 mg/kg/hr to the patient one to eight hours before surgery. As soon as is practical after the administration of anesthesia, a catheter is inserted endoscopically into the intestine, at the junction between the stomach and the proximal duodenum. The intestine is flushed with a saline solution supplemented with a dose of anti-trypsin/chymotrypsin at a flow rate of 0.1 to 10 mg/ml/hr, and then throughout the surgical procedure at a flow rate 0.02 to 0.5 liters/min.

The inventors have now discovered that the previously contemplated dosages are under most circumstances insufficient for treatment of acute and/or developing shock. In contrast, and especially where the rapid delivery of the protease inhibitor is via nasogastric (NG) tube into the stomach at high dosages, rapid treatment of acute and/or developing shock is now possible.

Figure 1B:
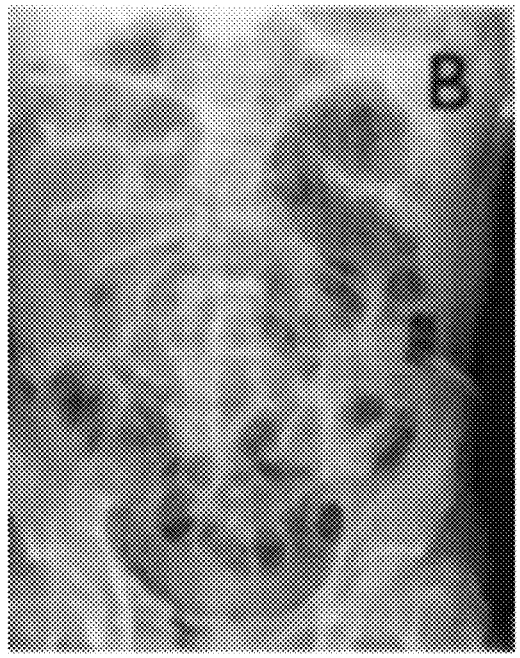
FIG. 1B is an X-ray of the abdomen of the patient on day 1 showing diffuse ileus and thickening of the intestinal wall.
Figure 1C:
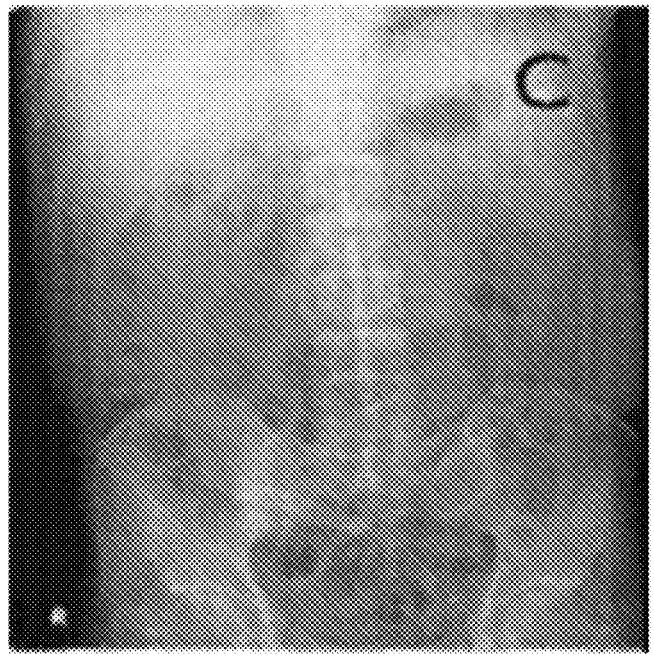
FIG. 1C is an X-ray of the abdomen of the patient on day 16 showing improved ileus.
Figure 1D:
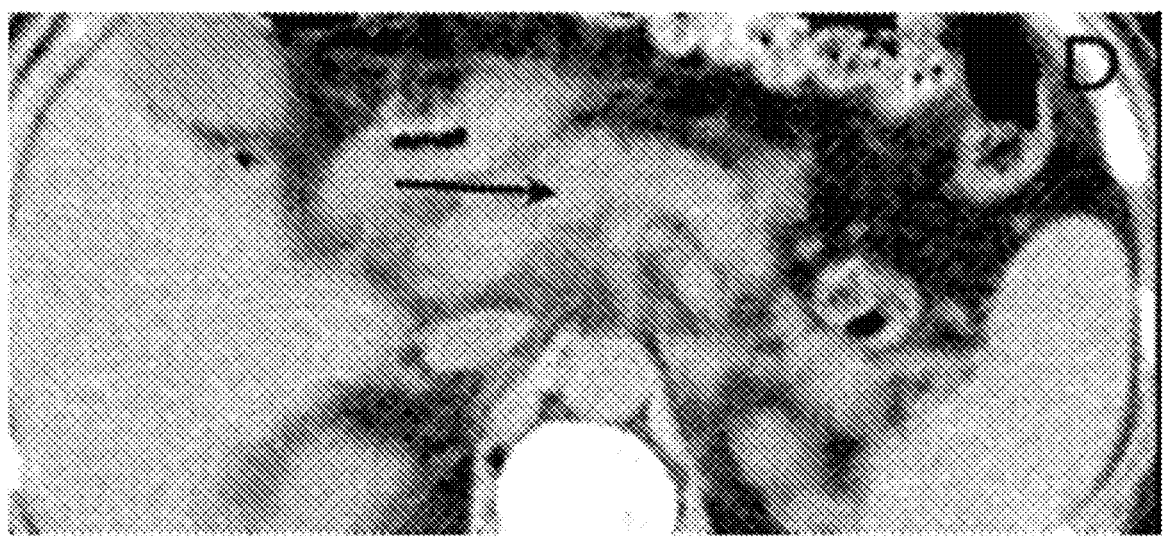
FIG. 1D is a CT scan of the abdomen of the patient on day 1 without contrast showing isodensity between pancreas (small arrow) and liver, which is inconsistent with pancreatic inflammation.

For example, as reported in a case study from the Cheng-Hsin General Hospital (that was approved by Human Ethics Committee and written consent by the patient), a 58-years old male heart transplant patient was regularly followed-up in the clinic with cyclosporine, mycophenolate, and prednisolone therapy for four years. The cyclosporine level was kept around 150 . . . 200 mg/dL without evidence of rejection or infection during this period of follow-up. Before admission, the patient had a motorcycle accident and perineum trauma. The wound was self-managed by the patient and deteriorated after one week. He was hospitalized and immediately admitted to the intensive care unit. At presentation, blood pressure was 80/40 mmHg in spite of aggressive fluid management with 2 liters of crystalloid and colloid fluid over 5 hours and vasopressor therapy with dopamine 5 kg/kg/min. Emergent surgical debridement over perineum was carried out but the clinical condition did not improve. He was intubated and received broad-spectrum antibiotics, including teichomycin, meropenem, and caspofungin. The blood chemistry of amylase and lipase values kept raising as can be readily taken from FIG. 1A (measurement units are: Amylase: IU/ml; Lipase: IV/ml; WBC: x 10 411), and an x-ray of the abdomen showed dilated small intestine with ileus as seen in FIG. 1B. At the same time, a CT of the abdomen did not showed edema and fluid accumulation over the pancreatic area as can be seen in FIG. 1D. The diagnosis was Fournier's gangrene complicated with septic shock and multiple organ failure. Due to persistent septic shock and worsening septic markers, the patient received in addition a diverting colectomy and intravenous total parental nutrition. Furthermore, the patient also received a second wide debridement. The wound culture was positive with multiple drug resistance *Pseudomonas aeruginosa* and *Bacteroides* thetaiotaomicron.

Intravenous gabexate mesilate was given for severe septic shock and elevated amylase and lipase values (as markers for presence of pancreatic enzymes) at a dose of 3000 mg/day. At the same time, the patient stopped all enteral feeding and total parental nutrition was given with positive fluid balance of more than 1 liter per day. But these therapies did not reduce plasma amylase and lipase values over the next 12 hours, and instead both values still kept rising.

Treatment was then switched to enteral gabexate mesilate infusion by continuous feeding into the stomach via nasogastric tube at a dose of 3000 mg/day in 2000 ml of normal saline. Within a period of two days the blood pressure stabilized with minimal dose of dopamine, the glucose level could be controlled by reduced dose of subcutaneous insulin, and the patient's level of conscience increased. On the third day, the dose of gabexate mesilate was reduced to 300 mg/day in a fluid volume of 2000 ml and kept at this level for 10 days before discharge of the patient from the intensive care unit. The amylase, lipase and white blood cell (WBC) count reduced to control values (see FIG. 1A) and x-ray of the abdomen showed an improved ileus as can be taken from FIG. 1C. Three days after enteral gabexate mesilate treatment he was extubated. On day 13, the immunosuppressant medication was restored with reduced dosage compared to the time before hospitalization and he was discharged from the ward after one month of admission. Five months after discharge at the time of this report writing the patient was alive.

Thus, it should be appreciated that a developing and even acute shock condition in a mammal (and especially human) can be treated upon diagnosis of the mammal/human with the shock condition by administration of a therapeutically effective amount of a protease inhibitor in a liquid formulation at a dosage of at least 20 mg/kg (e.g., 400 mg in 2 liter of fluid into the stomach to an average adult over a period of 24 hrs), wherein the liquid formulation is administered to a location in a gastrointestinal tract, wherein the location is upstream of another location at which pancreatic proteases are released into the gastrointestinal tract, and wherein the liquid formulation is administered under a protocol effective to treat the shock and potential multi-organ failure from the location. While it is not excluded that at least some of the therapeutic effect is derived from passage of the liquid formulation into and throughout the small intestine, it is noted that the treatment according to the inventive subject matter does not require administration of the liquid formulation to the small intestine, which significantly facilitates treatment and increases speed. Consequently, it should be noted that the liquid formulation can be administered directly to the stomach via nasogastric tube, catheter, direct injection, or even via a drink where the patient's condition allows such administration.

Therefore, and viewed from a different perspective, the inventors contemplate the use of a protease inhibitor in the manufacture of a medicament for treatment of shock and/or multi-organ failure due to shock in a mammal, wherein the protease inhibitor is formulated in liquid formulation to allow at least once daily administration to the stomach of the mammal at a dosage of at least 20 mg/kg and in an amount that provides at least 2 g of the protease inhibitor per day. Consequently, the inventors also contemplate a protease inhibitor for use in treating developing or acute shock and/or multi-organ failure due to shock in a mammal, wherein the protease inhibitor is formulated in a liquid solution to allow administration to the stomach at a dosage of at least 20 mg/kg and in an amount that provides at least 2 g of the protease inhibitor per day.

With respect to ascertaining that a patient is developing a shock condition and/or has acute shock, it should be noted that the shock condition and/or organ failure may be due to a variety of causes. For example, especially contemplated conditions include traumatic, septic, or cardiogenic shock, shock due to surgical complications, or shock due to complications from radiation and/or chemotherapy treatment, organ perforation, chylothorax, pre-treatment for surgery (e.g., aortic reconstruction), severe bacterial infections (e.g., Fourniers gangrene and other cSSTIs, infections related to pneumonia, sepsis and/or bacteremia, community, health care associated and/or hospital acquired infections), and damage from mechanical ventilators, or dialysis.

Consequently, the manner of diagnosing may vary considerably, and it is generally contemplated that all known diagnostic manners are deemed suitable herein and include measurement of enzymatic activity in various biological fluids, and especially in arterial or venous plasma, peritoneal or thoracic lavage fluid, and/or lymphatic fluid. Among other suitable biochemical markers, especially preferred enzymatic activities are those from amylase, trypsin, chymotrypsin, kallikrein, elastase, MMP, lipase, and other digestive enzymes and mediators that enter the circulatory system as a result of developing or acute shock. Alternatively, or additionally, the developing or acute shock condition may also be ascertained by measurement and/or identification of various volatile compounds as described in WO2010/087874, which is incorporated herein.

With respect to suitable quantities of one or more protease inhibitors, the inventors observed in various animal models that shock treatment using protease inhibitors to block digestive enzymes requires for at least some protease inhibitors a minimum effective dosage that is substantially above the dosage contemplated in the '283 patent. For example, using tranexamic acid in rats, the minimum effective dose was 100 mg/kg (127 mM in the enteral solution with 17 ml to a 350 gm rat). Here, tranexamic acid was given to rats in 18 cc of fluid. The equivalent concentration in 2 liters (deemed suitable as human dose) is 3.2 grams. The maximum dose tested in rats was 1125 mg/kg, which is equivalent to 36 grams for a human dose in 2 liters of fluid to be administered into the lumen of the stomach or intestine.

Consequently, it is generally preferred that in human, administration is performed as a single dose/day (e.g., 2 to 4 grams of Foy in 1 to 2 liter solution with GOLYTELY® (PEG) or saline) over multiple days (up to 14) given via NG tube, which has shown to be very effective.

It should therefore be appreciated that the inventors contemplate administration of one or more protease inhibitors, and especially a serine protease inhibitor for treatment of developing or acute shock (e.g., septic, cardiogenic, traumatic) where the protease inhibitor is administered in an aqueous pharmaceutically acceptable carrier (e.g., saline, isotonic PEG solution, etc.) at a dosage of at least 20 mg/kg, at least 30 mg/kg, at least 40 mg/kg, at least 50 mg/kg, at least 60 mg/kg, at least 70 mg/kg, at least 80 mg/kg, at least 90 mg/kg, at least 100 mg/kg, and even higher. As used herein, the expression "mg/kg" refers to milligram of the protease inhibitor (or other active compound) in the administered composition per kilogram of patient body weight. Thus, the enumerated quantity is specific to the formulation as administered, rather than to an absorbed or bioavailable quantity of the inhibitor (or other compound) in the patient. Alternatively, or additionally, the administration of suitable protease inhibitors is also contemplated to be an effective prophylactic measure and administration in such case would preferably be oral at a dosage of at least 20 mg/kg, more preferably at least 30 mg/kg, even more preferably at least 50 mg/kg, and most more preferably at least 100 mg/kg. Thus, administration may be in a dosage range of between 20-40 mg/kg, more preferably between 40-60 mg/kg, even more preferably between 60-80 mg/kg, and most more preferably between 80-100 mg/kg. Depending on the specific type of protease inhibitor, the concentration will thus be preferably be between 0.5 mM to 50 mM if given enteral or peritoneal. Where (additional) protease inhibitors are provided by IV, suitable dosage ranges will typically be between 5 and 500 mg/kg. Viewed from another perspective, the total dosage of protease inhibitors administered per day will preferably be at least 1 g, more typically at least 2 g, at least 4 g, and even as high as 10 g, as high as 20 g, and in some cases even higher. Pediatric total dosage will be correspondingly lower.

Depending on the severity of trauma, it is generally contemplated that higher dosages are more preferred for conditions with more severe trauma. For example, it is contemplated that hypovolemic shock treatment will require higher dosages than septic shock (e.g., at least 50-100 mg/kg vis-à-vis 20-50 mg/kg). It is further generally preferred that the administration is a single administration in a volume compatible with gastric administration. For example, the total volume of liquid formulation may be equal or less than 2 liter. In alternative aspects, suitable administration volumes include equal or less than 1 liter, equal or less than 0.5 liter, and equal or less than 0.25 liter. Alternatively, higher volumes may also be used, especially where administration is over an extended period, or continuous.

With respect to suitable schedules of administration it should be noted that the liquid formulations may be provided to the patient in a single dose or multiple doses per day and in some cases even continuously. Moreover, it is generally preferred that daily doses are administered over a period of several day, most typically between 2-21 days. However, it is generally preferred that administration is continued over at least 3 days, and more typically at least 7-10 days. Thus, suitable schedules include administration of contemplated compounds and compositions once daily, twice daily, three times daily, four times daily, or even more (or continuously) over at least two days, over a period of between three to seven days, or over a period of between 8 days to 14 days, and even longer (e.g., up to three weeks, four weeks, etc.). Still further, it should be noted that in addition to direct administration to the stomach, various parenteral routes may be employed (e.g., intravenous injection and/or intraperitoneal injection or lavage).

With respect to the protease inhibitor, it should be appreciated that all known and pharmaceutically acceptable protease inhibitors are deemed suitable for use herein, alone or in any reasonable combination. Especially suitable protease inhibitors include synthetic compounds such as 6-amidino-2-naphthyl p-guanidinobenzoate dimethanesulfate (ANGD), gabexate monomethanesulfonate (FOY), diisopropylfluorophosphate (DFP), p-(amidino-phenyl)methanesulfonyl fluoride (APMSF), tranexamic acid, and 4-(2-Aminoethyl) benzenesulfonyl fluoride (AEBSF), Camostate (FOY-305), and various native isolated or recombinant proteins with protease inhibitory activity such as serpins (e.g., SERPIN A1-A13, B1-13, Cl, etc.), alpha 1-antitrypsin, alpha 2 macroglobulin, etc. Thus, and viewed from a different perspective, it should be noted that serine protease inhibitors are expressly contemplated. However, various other inhibitors are also contemplated that have specificity for non-serine proteases, such as cysteine proteases, threonine proteases, aspartate proteases, glutamate proteases, and/or matrix metalloproteinases.

Additionally contemplated compounds with protease inhibitory activity include ACE inhibitors, one or more drugs that inhibits and/or renders digestive enzymes and/or resultant mediators inactive (which may be administered directly into the stomach, intestine and/or anus), various HIV protease inhibitors (e.g., saquinavir, ritonavir, indinavir, nelfinavir, amprenavir), certain diabetes drugs (e.g., JANUVIA®, sitagliptin; vildagliptin; alogliptin; saxagliptin), one or more DPP-IV inhibitors, ulinastatin, and MMP inhibitors (synthetic and natural such as TIMPs), and various antibiotics, including Imipenem, MERREM®, CIPRO®, Levoquin, TROVAN®, ZOSYN®, Tygasil, FORTAZ®, CLAFORAN®, ROCEPHIN®, Cefotetan, MEFOXIN®, Unaysn, Cefobid, Ancef, ZYVOX®, CUBICIN®, vancomycin type antibiotics etc and their generic equivalents. Therefore, it should also be appreciated that a second protease inhibitor may be administered, which may or may not be the same or of the same class, and which may or may not be directly administered to the stomach.

Depending on the particular protease inhibitor, it should be appreciated that the carrier may vary considerably. However, it is generally preferred that the carrier is an isotonic aqueous carrier that preferably contains electrolytes. Moreover, additional ingredients may include glycols, and especially PEG (e.g., polyethylene glycol-3350), and pharmaceutically acceptable co-solvents. Thus, contemplated inhibitors and other drugs may be suspended or dissolved in polyethyleneglycol or saline. For example, 0.5 to 2 liters may be directly administered to the stomach, and where given by IV, dripped from 3 to 10 hours (e.g., over 8 hours).

Furthermore, it is contemplated that additional pharmaceutically active agents may be administered to the patient, preferably at dosages and protocols already established. For example, suitable additional pharmaceutically active agents include various lipase inhibitors, amylase inhibitors, albumin, and/or cytotoxic lipid binding protein, all of which may be co-administered with the protease inhibitor or separately administered.

Moreover, the inventors have also discovered that use of an oxygen carrier (i.e., one or more chemical compounds which can carry and release oxygen) during treatment helped minimize the damage to the organs. Most preferably, oxygen carriers will be those that are suitable or deemed suitable as blood substitute. Consequently, especially suitable oxygen carriers include various perfluorocarbon-based carriers (e.g., oxygent, oxycyte, PHER-02, perftoran, etc.) and hemoglobin-based carriers (e.g., HEMOPURE®, OXYGLOBIN®, hemospan, POLYHEME®, dextran hemoglobin, hemotech, etc.), all of which are typically formulated as a liquid prior to oxygen loading.

Administration of oxygen directly into the lumen of the intestine is thought to minimize oxygen depletion, enhance ATP production in the mucosal barrier, and thereby preserve epithelial mucosal barrier function and enhance repair of the barrier after elevation of epithelial permeability. Consequently, such oxygen supplementation is thought to interfere with breakdown of the mucosal barrier in the stomach and the intestine under conditions of hypoxia and minimize escape of digestive enzymes and consequently destruction of tissue and generation of multi-organ failure. Thus, it is generally contemplated to deliver oxygen via an artificial oxygen carrier into the lumen of the intestine, either as preventive measure in anticipation of hypoxia in the intestine, or to minimize tissue hypoxia as acute or chronic intervention.

Therefore, and more generally viewed, an oxygen carrier may be used for treatment of developing or acute shock, to reduce multi-organ failure and mortality, for use in surgery in which blood flow to the intestine is intentionally or non-intentionally reduced, and for any form of intestinal complications associated with hypoxia. Remarkably, there is currently no method practiced in the art to maintain oxygen at the mucosal barrier during elective (e.g., surgery that requires interruption of blood flow to the intestine like vascular reconstructions, intestinal lesion resections, tumor resections, etc.) or non-elective clinical situations (due to trauma or disease related reductions of the blood flow to the intestine). And use of oxygen carriers may provide a simple solution for such problems.

For example, in a typical application during surgery or in the treatment of developing or acute shock, an artificial blood product capable to carry oxygen (e.g., oxygen carrier Perfluorodecalin (C10F18), CAS 306-94-5, 95% mixture of cis and trans isomers) is saturated with oxygen using well known methods and kept in an airtight container prior to surgery or treatment. The oxygen carrier solution can then be administered into lumen of the intestine orally, by NG tube into the stomach, or by catheter into the duodenum before or during intestinal ischemia and/or shock. R should be noted that perfluorodecalin was as an ingredient in Fluosol, an artificial blood product developed by Green Cross Corporation (Japan). In typical known uses, perfluorodecalin can be applied topically, to provide extra oxygen to a specific location, to accelerate wound healing. Moreover, organs and tissues can be stored for longer periods in oxygenated perfluorodecalin (e.g., the "two-layer method" uses perfluorodecalin and University of Wisconsin solution to preserve organs before their transplantation.

The inventors have demonstrated feasibility of such approach in a mammalian (rat) model with severe ischemic intestine in which enteral administration of an oxygen carrier served to minimize intestinal damage by prevention of the entry of digestive enzymes into the wall of the intestine. More specifically, the feasibility was illustrated in a model with 30 min ischemia with perfluorodecalin solution 17 ml for 230 g rat) previously saturated for 10 min in oxygen. Thus, it should be noted that gastric, duodenal, jejunal, and ileal irrigation (or otherwise exposure) may be used as a stand-alone or supplemental treatment in human and other mammals. Most typically, the volume of the oxygen carrier will be adjusted such as to allow intimate contact with the oxygen carrier throughout the stomach, duodenum, jejunum, and/or ileum.

Most typically, administration to a human will therefore be performed via oral administration, via gastric intubation, via catheter into the stomach and/or small intestine, etc. It should therefore be appreciated that the volume of the oxygen carrier per administration may vary considerably. However, it is generally preferred that the volume administered to a human is at least 100 ml, more typically at least 250 ml, even more typically at least 500 ml, and most typically at least 1000 ml. Administration may be performed as a single dose administration, or in multiple doses, or even continuously, and may be performed only once or over several days. Moreover, it should be appreciated that administration of the oxygen carrier may be performed together with the administration of the protease inhibitor, in an alternating schedule with the administration of the protease inhibitor, or separately from the administration of the protease inhibitor.

Where co-administration with a protease inhibitor is preferred, it should be especially appreciated that the protease inhibitor may be dissolved or dispersed in the oxygen carrier. Thus, an oxygen carrier solution is contemplated that will include a protease inhibitor at a concentration of between 0.5 and 50 mM (or even higher). Viewed from a different angle, an oxygen carrier solution may be formulated to allow administration of a protease inhibitor at a dosage of at least 20 mg/kg, at least 30 mg/kg, at least 40 mg/kg, at least 50 mg/kg, at least 60 mg/kg, at least 70 mg/kg, at least 80 mg/kg, at least 90 mg/kg, at least 100 mg/kg, and even higher. Thus, administration may be in a dosage range of between 20-40 mg/kg, more preferably between 40-60 mg/kg, even more preferably between 60-80 mg/kg, and most more preferably between 80-100 mg/kg. Viewed from another perspective, the total dosage of protease inhibitors in the oxygen carrier administered per day will preferably be at least 1 g, more typically at least 2 g, at least 4 g, and even as high as 10 g, as high as 20 g, and in some cases even higher. Pediatric total dosage will be correspondingly lower. Likewise, mixtures of an aqueous carrier with the protease inhibitor and the oxygen carrier are also expressly contemplated herein.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C and N, the text should be interpreted as requiring only one element from the group, not A plus N, or B plus N, etc.

What is claimed is:

1. A method of treating shock in a mammal in need thereof comprising orally administering to the mammal a therapeutically effective amount of a pharmaceutical composition comprising tranexamic acid and a liquid carrier, wherein the shock is caused by (i) a surgical intervention, (ii) a complication from radiation treatment, (iii) a complication from chemotherapy treatment, (iv) an organ perforation, (v) chylothorax, (vi) damage from a mechanical ventilator, or (vii) dialysis.

2. The method of claim 1, wherein the shock is caused by surgical intervention.

3. The method of claim 1, wherein the composition comprises about 2 grams to about 20 grams of tranexamic acid.

4. The method of claim 1, wherein the composition comprises about 0.16 wt % to about 1.80 wt % of tranexamic acid.

5. The method of claim 1, wherein the liquid carrier is an aqueous saline solution.

6. The method of claim 1, wherein the liquid carrier is an isotonic polyethylene glycol solution.

7. A method of treating shock in a mammal in need thereof comprising orally administering to the mammal a therapeutically effective amount of a liquid pharmaceutical composition comprising tranexamic acid, polyethylene glycol, and electrolytes; wherein the shock is caused by (i) a surgical intervention, (ii) a complication from radiation treatment, (iii) a complication from chemotherapy treatment, (iv) an organ perforation, (v) chylothorax, (vi) damage from a mechanical ventilator, or (vii) dialysis.

8. The method of claim 7, wherein the shock is caused by surgical intervention.

9. The method of claim 7, wherein the composition comprises about 2 grams to about 20 grams of tranexamic acid.

10. The method of claim 7, wherein the composition comprises about 0.16 wt % to about 1.80 wt % of tranexamic acid.

11. The method of claim 7, wherein the composition comprises an aqueous saline solution.

12. The method of claim 7, wherein the composition comprises an isotonic polyethylene glycol solution.

13. A method of treating shock in a mammal in need thereof comprising orally administering to the mammal a therapeutically effective amount of an aqueous pharmaceutical composition comprising a protease inhibitor and electrolytes; wherein the shock is caused by (i) a surgical intervention, (ii) a complication from radiation treatment, (iii) a complication from chemotherapy treatment, (iv) an organ perforation, (v) chylothorax, (vi) damage from a mechanical ventilator, or (vii) dialysis.

14. The method of claim 13, wherein the shock is caused by surgical intervention.

15. The method of claim 13, wherein the protease inhibitor is a serine protease inhibitor, a cysteine protease inhibitor, a threonine protease inhibitor, an aspartate protease inhibitor, a glutamate protease inhibitor, a matrix metalloprotease inhibitor, or a combination of two or more thereof.

16. The method of claim 13, wherein the protease inhibitor is a serine protease inhibitor.

17. The method of claim 13, wherein the protease inhibitor is a serpin, an alpha 1-antitrypsin, an alpha-2-macroglobulin, 6-amidino-2-naphthyl, p-guanidinobenzoate dimethanesulfate, gabexate monomethanesulfonate, diisopropylfluorophosphate, p-(amidinophenyl)methanesulfonyl fluoride, tranexamic acid, 4-(2-aminoethyl)benzenesulfonyl fluoride, or camostate.

18. The method of claim 13, wherein the composition comprises about 2 grams to about 20 grams of the protease inhibitor.

19. The method of claim 13, wherein the composition comprises 0.16 wt % to 1.80 wt % of the protease inhibitor.

20. The method of claim 13, wherein the composition has a volume of about 500 ml to about 1000 ml.

* * * * *